United States Patent
Duprat

[19]

[11] Patent Number: 6,007,542
[45] Date of Patent: Dec. 28, 1999

[54] DEVICE FOR FOLDING A FLEXIBLE INTRAOCULAR IMPLANT, AND FOR KEEPING IT FOLDED

[75] Inventor: Alain Duprat, Roquettes, France

[73] Assignee: Moria SA, Antony, France

[21] Appl. No.: 09/005,757

[22] Filed: Jan. 12, 1998

[51] Int. Cl.⁶ .................................................. A61B 17/28
[52] U.S. Cl. .......................................... 606/107; 606/205
[58] Field of Search ................................... 606/107, 166, 606/205, 1; 623/6

[56] References Cited

U.S. PATENT DOCUMENTS

| | | |
|---|---|---|
| 5,100,410 | 3/1992 | Dulebohn . |
| 5,171,241 | 12/1992 | Buboltz et al. .............................. 606/1 |
| 5,281,227 | 1/1994 | Sussman ................................. 606/107 |
| 5,290,293 | 3/1994 | Van Noy et al. . |
| 5,292,324 | 3/1994 | McDonald . |
| 5,454,818 | 10/1995 | Hambleton et al. ..................... 606/107 |

FOREIGN PATENT DOCUMENTS 0590201  10/1992  European Pat. Off. .

*Primary Examiner*—Michael Buiz
*Assistant Examiner*—Tan-Uyen T. Ho
*Attorney, Agent, or Firm*—Griffin, Butler, Whisenhunt & Szipl, LLP

[57] ABSTRACT

The present invention provides a device for folding a flexible intraocular implant and for keeping it folded, the device comprising two jaws, each jaw having an active surface forming a reentrant dihedral, and each being slidably mounted relative to the other jaw along a direction parallel to one of the faces of the reentrant dihedral, between a first position in which the jaws are in contact against each other via the ends of the faces parallel to the sliding direction, and at least one second position in which the jaws are moved apart from each other. At least one resilient member is coupled between the jaws and has the effect of tending to keep them in contact with each other. Each jaw is secured to a pushbutton situated facing its active surface and beyond the other jaw.

8 Claims, 2 Drawing Sheets

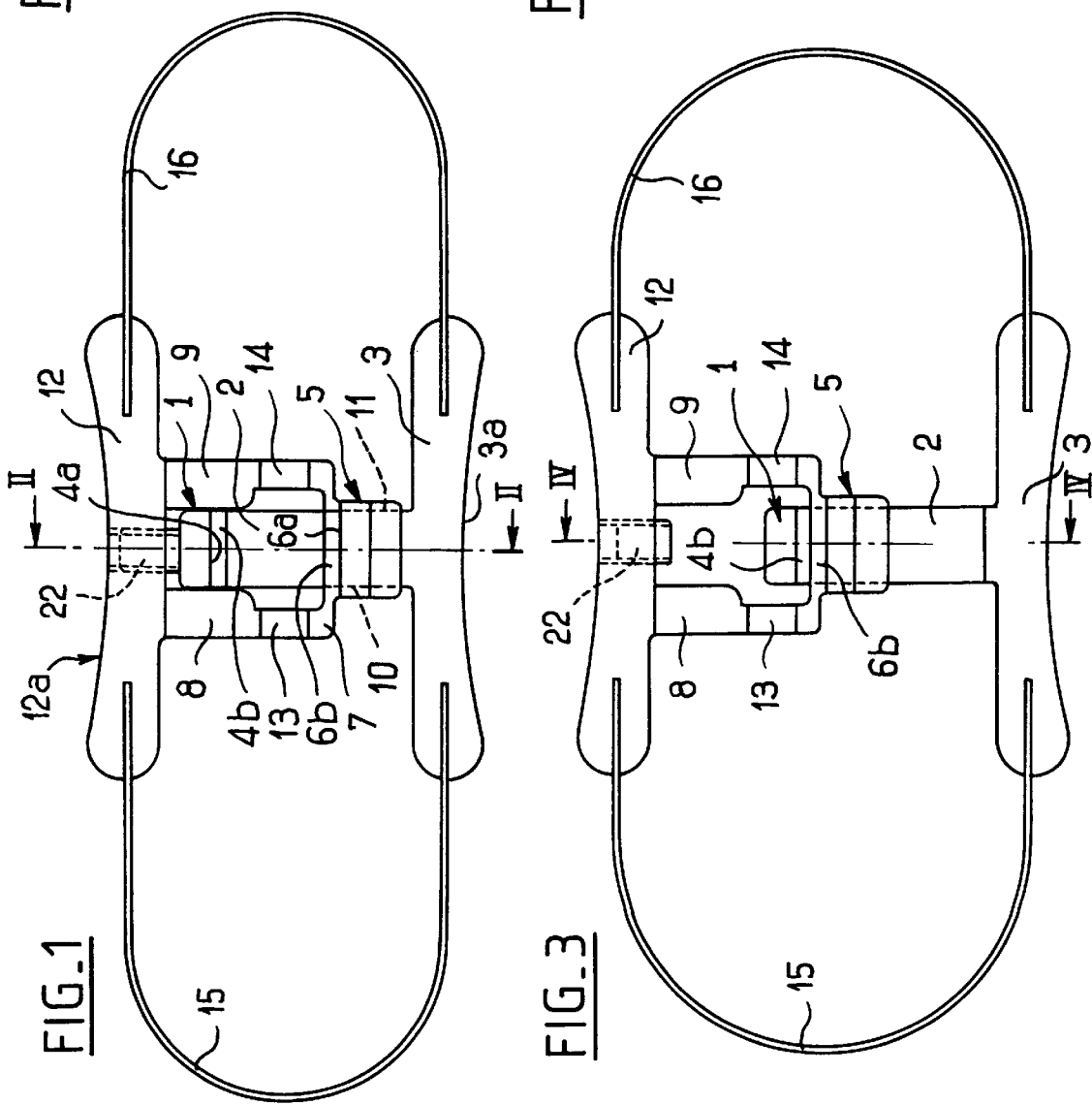

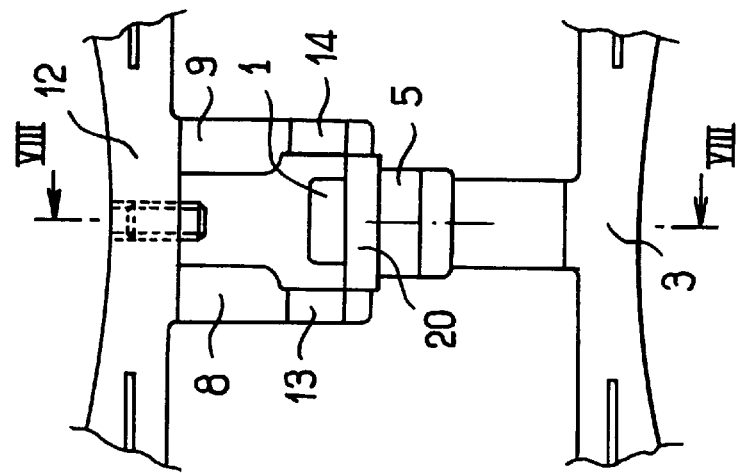
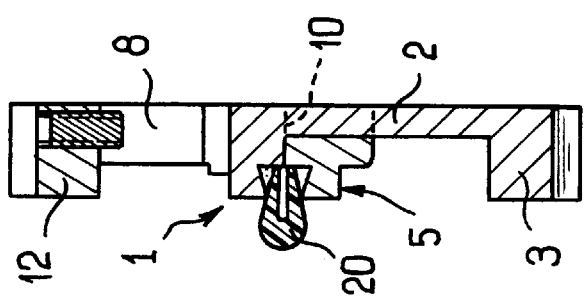
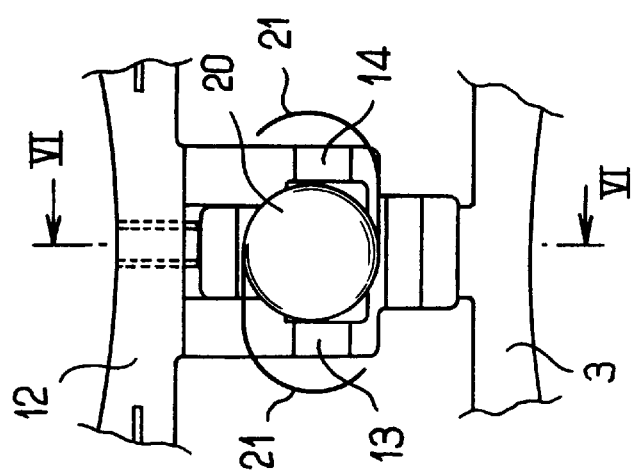
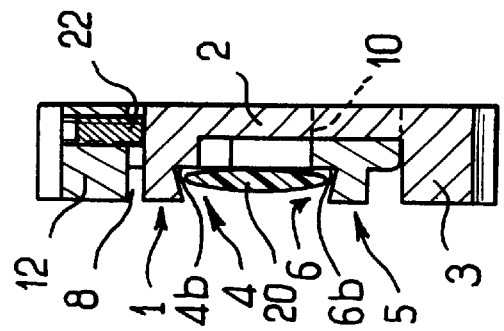

DEVICE FOR FOLDING A FLEXIBLE INTRAOCULAR IMPLANT, AND FOR KEEPING IT FOLDED

The present invention relates to a device for preparing a flexible implant, in particular an implant constituting an artificial lens, immediately before it is inserted in the eye.

BACKGROUND OF THE INVENTION

Flexible implants are being used more and more in operations to remove cataracts and to put an airtificial lens into place, such implants having the advantage that for insertion into the eye they require an incision of small size only. Once inserted, the implants unfold elastically and return to their initial lens shape inside the eye. To facilitate the work of the surgeon, it is advantageous to prepare the implant in advance and to keep it in its folded condition so that the surgeon only needs to take hold of it using appropriate forceps and insert it into the eye.

OBJECT AND SUMMARY OF THE INVENTION

The present invention proposes a device for performing that function, i.e. for folding the implant and holding it in the folded state ready for the surgeon.

To this end, the invention therefore provides a device for folding a flexible intraocular implant and for keeping it folded, the device comprising two jaws, each jaw having an active surface forming a reentrant dihedral, and each being slidably mounted relative to the other jaw along a direction parallel to one of the faces of the reentrant dihedral, between a first position in which the jaws are in contact against each other via the ends of the faces parallel to the sliding direction, and at least one second position in which the jaws are moved apart from each other by a distance not less than the diameter of the implant to be folded, while at least one resilient member is coupled between the jaws to have the effect of tending to keep them in contact with each other, each jaw also being secured to a pushbutton situated facing its active surface and beyond the other jaw.

The device behaves like a normally closed clamp which, when actuated by the operator, opens to leave a gap between its jaws for receiving an implant, and when the operator ceases to actuate it, recloses on the implant forcing it to take up a folded configuration. While in this state, the jaws hold the implant in the folded condition, even after the operator has ceased to act. The fold zone of the implant projects forwards from the jaws, thus making it possible to take hold of the folded implant using appropriate forceps, specifically for inserting the implant in the eye of the patient.

In an embodiment, one of the jaws is carried by the central portion of a cross-member belonging to a stirrup piece, with the other jaw extending between the uprights of the stirrup piece, the ends of the uprights remote from their ends carrying the cross-member being fitted with the corresponding pushbutton. In this way, the uprights of the stirrup piece can constitute means for centering the implant between the jaws when the jaws are in the open state.

BRIEF DESCRIPTION OF THE DRAWINGS

Other characteristics and advantages appear from the following description of an embodiment of the invention.

Reference is made to the accompanying drawings, in which:

FIG. 1 is a plan view showing the device of the invention in its open state ready to receive an implant;

FIG. 2 is a section view on plan II—II of FIG. 1;

FIG. 3 is a plan view of the device in its closed state in the absence of an implant;

FIG. 4 is a section view on line IV—IV of FIG. 3;

FIG. 5 is a fragmentary view of the FIG. 1 device with an implant ready to be folded in half;

FIG. 6 is a section view on plane VI—VI of FIG. 5;

FIG. 7 is a fragmentary view of the device of the invention holding an implant folded between its jaws; and FIG. 8 is a section view on VIII—VII of FIG. 7.

MORE DETAILED DESCRIPTION

The device shown in the figures has a first jaw 1 carried by one of the ends of a finger 2, with the other end of the finger 2 being fitted with a pushbutton 3. The pushbutton is in the form of a bar extending substantially perpendicularly to the finger 2 and it has a concave outside surface 3a.

The jaw 1 has an active surface 4 defined by the faces 4a and 4b of a reentrant dihedral facing the pushbutton 3. The face 4b defines a surface that is substantially parallel to the longitudinal axis of the finger 2. The active surface 4 faces towards the pushbutton 3.

The device also has a second jaw 5 which, like the jaw 1, has an active surface 6 defined by the faces 6a and 6b of a reentrant dihedral facing the reentrant dihedral of the jaw 1. The jaw 5 is carried by the middle portion of the cross-member 7 of a stirrup piece whose uprights 8 and 9 are on opposite sides of the finger 2 carrying the jaw 1. Behind the jaw 5, the cross-member 7 has flaps 10 and 11 defining a guiding slideway for the finger 2 on either side thereof in like manner to the uprights 8 and 9 of the stirrup piece. The ends of the uprights 8 and 9 remote from the cross-member 7 are fitted with a pushbutton 12 in the form of a bar like the pushbutton 3 and it too has a concave. outside surface 12a. The active surface 6 of the jaw 5 faces towards the pushbutton 12.

The surfaces 4b and 6b of the jaws 1 and 5 occupy a common plane parallel to the plane of relative sliding between the finger and the stirrup piece and they define a support plane for the implant to be folded. Between the pushbutton 12 and the cross-member 7, each of the uprights 8 and 9 has a respective forward projection 13 or 14 that projects a little way in front of the plane which contains the faces 4b and 6b of the active surfaces 4 and 6 of the jaws.

Two spring blades 15 and 16 extend between the ends of the pushbuttons 3 and 12, each spring blade having one end received in each pushbutton. The spring blades serve firstly to hold the two portions of the device carrying the jaws 1 and 5 in sliding engagement one within the other, and secondly to urge the pushbuttons ressiliently away from each other by constantly urging the jaws 1 and 5 to press against each other in the position shown in FIG. 3. In this position, the jaws are in abutment against each other via the limiting edges of their respective faces 4b and 6b of their active surfaces, as shown in FIG. 4.

It will be understood from these figures that when the operator pushes the pushbuttons 3 and 12 towards each other between the thumb and the index finger of one hand, the pushbuttons move towards each other, thereby separating the jaws 1 and 5. As shown in FIGS. 5 and 6, an implant 20 can then be placed between the jaws with the implant resting in part on the faces 4b and 6b of the jaws and in part against the front surfaces of the uprights 8 and 9 where they are situated at the same level, with the sides of the implant being held between the jaws by the projections 13 and 14. In conventional manner, the intraocular implant may have flexible loops 21, which loops can be disposed as shown in FIG. 5 or else in a position perpendicular to the position shown, each thus passing to one side of a jaw. When the operator relaxes grip on the pushbuttons, the spring blades 15 and 16 cause the jaws to move towards each other, thereby deforming the implant 20 as shown in FIGS. 7 and 8. The implant is thus folded in half, with the fold projecting forwards from the jaws so as to form a portion whereby the folded implant can be taken hold of by appropriate forceps, and the implant is kept in the folded state by the return force of the spring blades 15 and 16, thereby enabling the operator to release the device which constitutes a support for a folded implant.

When the implant is to be inserted into the eye, using appropriate forceps, the portion of the implant 20 projecting in front of the jaws 1 and 5 is taken hold of and the jaws are relaxed by pushing the pushbuttons 3 and 12 towards each other, thereby enabling the implant to be taken away while being held in the folded state by the forceps holding it.

Finally, it can be seen in the figures that there is an abutment 22 which limits the opening stroke of the jaws. This abutment, e.g. constituted by a screw, can be adjustable so as to enable the spacing between the jaws to be matched to the size of the implant.

The device of the invention can be made out of various materials. If the device is to be reusable, then it is preferable for it to be made of titanium alloy, of stainless steel, or of some other analogous alloy known in the field of surgical implementation, thereby enabling it to be subjected to sterilization. If the device is for single use only, then it can be made of injected plastics material, at least for the two pushbutton-and-jaw assemblies, with the injected pieces having housings in the ends of the pushbuttons for receiving the spring blades which may likewise be made of plastics material or else of metal.

I claims:

1. A device for folding a flexible intraocular implant and for keeping it folded, the device comprising two jaws, each jaw having an active surface forming a reentrant dihedral, and each being slidably mounted relative to the other jaw along a direction parallel to one of the faces of the reentrant dihedral, between a first position in which the jaws are in contact against each other via the ends of the faces parallel to the sliding direction, and at least one second position in which the jaws are moved apart from each other, the device including at least one resilient member coupled between the jaws and having the effect of tending to keep them in contact with each other.

2. A device according to claim 1, wherein each jaw is secured to a pushbutton situated facing its active surface and beyond the other jaw.

3. A device according to claim 2, wherein one of the jaws is carried by the central portion of a cross-member belonging to a stirrup piece, with the other jaw extending between the uprights of the stirrup piece, the ends of the uprights remote from their ends carrying the cross-member being fitted with the corresponding pushbutton.

4. A device according to claim 3, wherein the uprights of the stirrup piece include means for holding the sides of the implant relative to the jaws when the jaws are held apart in their second position.

5. A device according to claim 3, wherein the other jaw is carried by one of the ends of a finger slidably mounted relative to the stirrup piece behind the corresponding jaw, the other end of the finger being provided with the corresponding pushbutton.

6. A device according to claim 3, wherein each pushbutton is constituted by a bar extending transversely respectively relative to the finger and to the stirrup piece, with the outside face of each bar being concave.

7. A device according to claim 6, wherein the resilient member is constituted by two spring blades each forming a spring clip interconnecting the pushbutton bars.

8. A device according to claim 1, including an abutment limiting the spacing of the jaws to a maximum value.

* * * * *